United States Patent
Grebeniuk et al.

(10) Patent No.: US 12,146,128 B2
(45) Date of Patent: Nov. 19, 2024

(54) PHOTOPOLYMERISED CELL CULTURE DEVICES

(71) Applicant: Katholieke Universiteit Leuven, Leuven (BE)

(72) Inventors: Sergii Grebeniuk, Kiev (UA); Adrian Ranga, Ixelles (BE)

(73) Assignee: Katholieke Universiteit Leuven, Leuven (BE)

( * ) Notice: Subject to any disclaimer, the term of this patent is extended or adjusted under 35 U.S.C. 154(b) by 864 days.

(21) Appl. No.: 17/253,803

(22) PCT Filed: Jun. 26, 2019

(86) PCT No.: PCT/EP2019/067042
§ 371 (c)(1),
(2) Date: Dec. 18, 2020

(87) PCT Pub. No.: WO2020/002451
PCT Pub. Date: Jan. 2, 2020

(65) Prior Publication Data
US 2021/0269757 A1  Sep. 2, 2021

(30) Foreign Application Priority Data

Jun. 26, 2018 (GB) .................................... 1810447

(51) Int. Cl.
*C12M 3/06* (2006.01)
*C12M 1/12* (2006.01)
*C12M 1/26* (2006.01)

(52) U.S. Cl.
CPC ............ *C12M 23/16* (2013.01); *C12M 25/14* (2013.01); *C12M 33/00* (2013.01)

(58) Field of Classification Search
None
See application file for complete search history.

(56) References Cited

U.S. PATENT DOCUMENTS

| 4,575,330 A | 3/1986 | Hull | |
|---|---|---|---|
| 2008/0261288 A1* | 10/2008 | Gonda | C12M 25/14 435/174 |
| 2011/0081664 A1* | 4/2011 | Forbes | C12M 25/02 435/325 |

(Continued)

FOREIGN PATENT DOCUMENTS

| CN | 102373153 A | * | 3/2012 | ............ C12M 23/16 |
|---|---|---|---|---|
| WO | 2010096469 A2 | | 8/2010 | |

(Continued)

OTHER PUBLICATIONS

Kolesky et al., Three-dimensional bioprinting of thick vascularized tissues, Mar. 22, 2016, PNAS, vol. 113 No. 12, pp. 3179-3184 (including Supporting Information provided by publisher) (Year: 2016).*

(Continued)

*Primary Examiner* — Holly Kipouros
(74) *Attorney, Agent, or Firm* — Dinsmore & Shohl LLP (57) ABSTRACT

The invention relates to devices for the culture of cellular aggregates, the device comprising abase plate (1) with inlet (21) and outlet (22) openings for delivery and removal of media wherein inlet and outlet openings are in fluidic connection with respectively inlet and outlet ports in the base plate, and comprising a plurality of channels of a biocompatible liquid- and gas-permeable material, wherein each of said channels is connected at one end to an inlet opening and at the other end to an outlet opening, characterized in that each channel extends at one end (31) upwards from the inlet opening, and extend at the other end upwards (32) from the outlet opening.

12 Claims, 5 Drawing Sheets

(56) References Cited

U.S. PATENT DOCUMENTS

| | | |
|---|---|---|
| 2016/0002368 A1 | 1/2016 | Gulino et al. |
| 2018/0002658 A1* | 1/2018 | Miller .................. C12N 5/0068 |
| 2021/0214662 A1* | 7/2021 | Hoying .................. C12M 23/16 |

FOREIGN PATENT DOCUMENTS

| | | |
|---|---|---|
| WO | 2014197999 A1 | 12/2014 |
| WO | 2016141137 A1 | 9/2016 |

OTHER PUBLICATIONS

Truong et al., Photopolymerizable hydrogels for tissue engineering applications, 2002, Biomaterials 23, pp. 4307-4314 (Year: 2002).*

Hinton et al., 3D bioprinting from the micrometer to millimeter length scales: Size does matter, 2017, Current Opinion in Biomedical Engineering, 1:31-37 (Year: 2017).*

Written Opinion in reference to co-pending European Patent Application No. PCT/EP2019/067042 filed Jun. 26, 2019.

International Search Report in reference to co-pending European Patent Application No. PCT/EP2019/067042 filed Jun. 26, 2019.

Bertassoni, et al., "Hydrogel Bioprinted Microchannel Networks for Vascularization of Tissue Engineering Constructs", Lab. Chip, vol. 13, pp. 2202-2211, Jul. 7, 2014.

Crivello, et al., "Photopolymer Materials and Processes for Advanced Technologies", Chemistry of Materials, vol. 26, pp. 533-548, 2014.

Deubel, et al., "Direct laser writing of three-dimensional photonic-crystal templates for telecommunications", Nature Materials, vol. 3, pp. 444-447, Jul. 2004.

Kolesky, et al., "Three-dimensional bioprinting of thick vascularized tissues", CrossMark, vol. 113, No. 12, pp. 3179-3184, Mar. 22, 2016.

Selimis, et al., "Direct laser writing: Principles and materials for scaffold 3D printing", Microelectronic Engineering, vol. 132, pp. 83-89, 2015.

* cited by examiner

PHOTOPOLYMERISED CELL CULTURE DEVICES

CROSS-REFERENCES TO RELATED APPLICATIONS

This application is a national-stage entry under 35 U.S.C. § 371 of International Application PCT/EP2019/067042, filed Jun. 26, 2019, which International Application claims the benefit of priority to Great Britain Patent Application No. 1810447.1, filed Jun. 26, 2018.

BACKGROUND OF THE INVENTION

Typical prior art culture devices which mimic a vascular network have a plurality of vessels extending laterally from an inlet port to an outlet port (e.g. WO2016141137). Different variations on this concept exist whereby for example vessels bifurcate at the inlet port and merge again at the outlet port.

Prior art vessels typically have a diameter of more than 150 µm [WO2010096469; Kolesky et al. (2016) *Proc. Natl. Acad. Sci* 113, 3179-3184; Bertassoni et al. (2014) *Lab Chip* 14, 2202-2211] which is large enough to fabricate such vessels without risk of breaking or of bending to an extent that the flow of medium is blocked.

Stereolithographic printing of culture devices allows to print vessels with an internal diameter as small as 5 µm. Printing methods wherein channels are printed in a horizontal orientation, in analogy to prior art designs, result in vessels wherein the lumen is typically blocked or more narrow than designed or programmed. There is a need for better methods and devices wherein photo-lithographic methods are used to produce culture devices with vascular networks.

SUMMARY OF THE INVENTION

An important problem encountered in stereo-lithographic processes is that the axial (vertical) resolution of the fabrication is approximately an order of magnitude lower that the lateral (horizontal) resolution. In order to achieve 5 µm resolution of the process, a high numerical aperture objectives should be used which dramatically increases costs of equipment and significantly decreases an overall speed of fabrication due to a small field of view and small polymerization spot (voxel) formed by such objectives. Furthermore, for the materials whose refractive index increases upon polymerization (which is the case for PEG-based hydrogels, for example), the actual axial resolution is much lower than theoretically predicted for homogenous media.

The specifics of the tissue vascularization problem, demands the diameter of the channels to be as small as possible in order to provide sufficient space for growing tissue and without interfering with normal tissue development. The typical diameter of the capillary is about 10 µm with the wall thickness of few micrometers. To be able to reliably fabricate tubular structures with an internal diameter of between 5 to 20 µm from hydrogels, numerical apertures higher than 1 would be needed. This results in very high costs since the objectives (N25x-APO-MP—25x Nikon CFI APO LWD Objective, 1.10 NA, 2.0 mm WD cost about 25,000 USD), or very small field of view (<300 µm) and very short working distance (<200 µm).

The methods of the present invention provides an optimized geometry of the micro-capillary grid which allows to use low numerical aperture optics while keeping high speed and reliability of the stereo-lithographic process.

In summary, the basic principle of the invention of the improved geometry resides in the creation of vertically printed channels, with typically an inverse U shape, wherein the channels are connected with inlet and outlet openings which are adjacent to each other.

The invention is further summarized in the following statements:

1. A device for the culture of cellular aggregates, the device comprising a base plate (1) with inlet (21) and outlet (22) openings for delivery and removal of media wherein inlet and outlet openings are in fluidic connection with respectively inlet and outlet ports in the base plate, and comprising a plurality of channels of a biocompatible liquid- and gas-permeable material, wherein each of said channels is connected at one end to an inlet opening and at the other end to an outlet opening, characterized in that each channel extends at one end (31) upwards from the inlet opening, and extend at the other end upwards (32) from the outlet opening.
2. The device according to statement 1, wherein channels (31, 32) extend vertically upwards from the base plate.
3. The device according to statement 1 or 2, wherein the channels have an inverse U-shape conformation.
4. The device according to any one of statements 1 to 3, further comprising reinforcements (8) between channels.
5. The device according to any one of statements 1 to 4, further comprising re-enforcing structures (6) surrounding the channels.
6. The device according to any one of statements 1 to 5, wherein the biocompatible liquid- and gas-permeable material is a photopolymerised hydrogel.
7. The device according to any one of statements 1 to 6, wherein the plurality of channels form a network with a volume between 0.1 mm$^3$ to 5 cm$^3$ mimicking a vascular network.
8. The device according to any one of statements 1 to 7, wherein the channels have an internal diameter of between 5 and 200 µm, 25 to 75 µM or 40 to 60 µM.
9. The device according to any one of statements 1 to 8, wherein the base plate is attached to a support (5), wherein channels for the supply and removal of liquids are in fluidic connection with outlet and inlet ports on the base plate.
10. The device according to any one of statements 1 to 9, wherein the attachment of the base plate and the support is obtained via crosslinking between the material of the base plate and the material of the support.
11. The device according to any one of statements 1 to 10, wherein the attachment of the base plate and the support is obtained via a male-female locking mechanism, wherein locking results from the swelling of the male part upon hydration in aqueous environments such as cell culture media.
12. A method for preparing a device for the culture of cellular aggregates by a stereolithographic printing process, the method comprising the steps of: printing a base plate (1) comprising plurality of inlet openings (21) on the top of the base plate, and a plurality of outlet openings (22) on a top section of the base plate, printing on the base plate upwards extending hollow channels (31, 32) which are at the bottom end in fluidic connection with the inlet and outlet openings, printing at the top end of a channel (31) extending from an inlet opening (21) and the top end of a channel (32) extending from an outlet opening (22) a connection (4), thereby bringing a pair of channels (31, 32) in fluidic connection with each other, forming a single, thereby forming a plurality of channels with, each channel allowing the passage of a liquid from an inlet opining to an outlet opening.

13. The method according to statement 12, wherein channels are formed which have an inverse U shape configuration.

14. The method according to statement 12 or 13, further comprising printing one or more walls or shell-like structure (6) (these can be perforated or grid like) on the base plate. Typically, walls are layer by layer printed together with the layer by layer assembly of the channels)

15. The method according to any one of statements 12 to 14, wherein reinforcements elements (8) are printed in between channels, between channels and base plate, or between channels and walls.

16. The method according to any one of statements 12 to 15, wherein the base plate is formed on a support (5) and comprises the steps of mounting a support comprising crosslinkable groups in a chamber filled with prepolymer, where the material of the support has chemical groups available for crosslinking with the prepolymer during the fabrication process, and printing the first layer of the base plate on the surface of the support thereby crosslinking the support with base plate.

SHORT DESCRIPTION OF THE FIGURES

FIG. 1A shows a base plate (1) with inlet openings (21) and outlet openings (22). [channels connecting inlet and outlet openings to respectively inlet and outlet ports are not shown]

FIG. 1B shows partially assembled channels (31, 32) raising upwards from the inlet (21) and outlet (22) openings.

FIG. 1C shows an assembled cell culture device wherein connections (4) connect extending tubes (31) and (32).

FIG. 2A shows the entire device. In FIG. 21, the channels are not shown to more clearly depict the basket.

FIG. 7A: size view; FIG. 7B: top view.

orientation showing one side and the top of the device. FIG. 8B orientation showing one side and the top of the device.

DETAILED DESCRIPTION OF THE INVENTION

Figure 1:
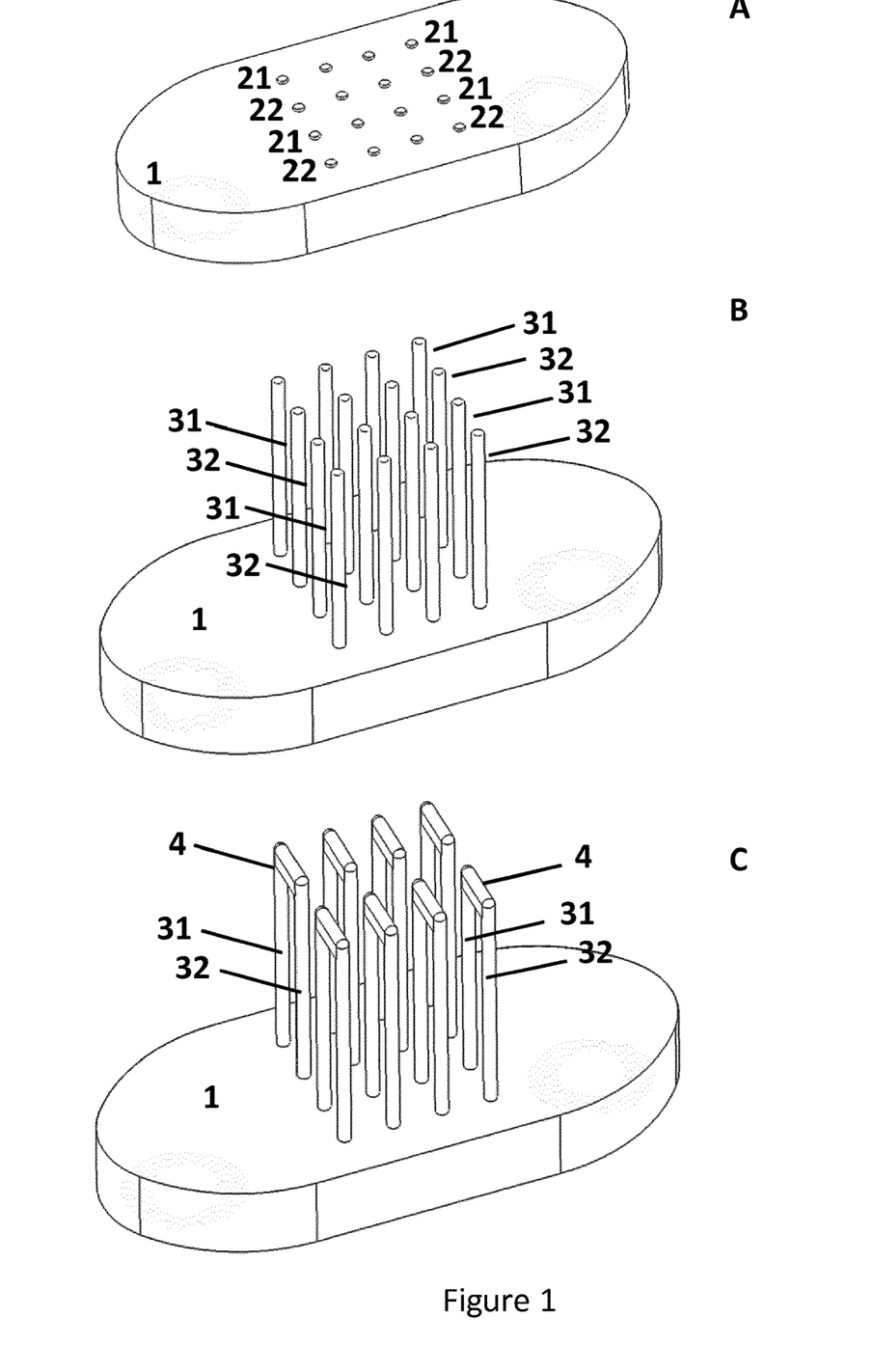
FIG. 1 shows the stepwise assembly of a cell culture device.

In the present invention, "top", "bottom", "vertical", "horizontal", "vertical" "upwards", "downwards" and the like refer to a configuration as depicted in FIG. 1, with base plate (1) as an horizontal bottom element.

Reference signs are provided with as sole function is to make claims easier to understand. They should not be seen as limiting the extent of the matter protected by the claims.

As mentioned above in the summary, the invention relates to the creation of a cell culture device with upward (typically vertically) printed channels, with typically an inverse U shape, wherein the channels are connected with inlet and outlet openings which are adjacent to each other on a base plates.

The concept of the invention is illustrated by the figures which show certain embodiment of the methods and devices as claimed. The figures serve as examples of the invention as defined in the claims.

FIG. 1 shows intermediate steps in the assembly of a cell culture device of the present invention.

FIG. 1A shows an example of a base plate (1) which has the function to distribute medium from one or more inlet ports (not shown) to a plurality of inlet openings (21). Similarly the base plate contains a plurality of outlet openings (22) to collect medium to an outlet port. The medium is directed to a waste or recirculated to the inlet port.

Figure 7:
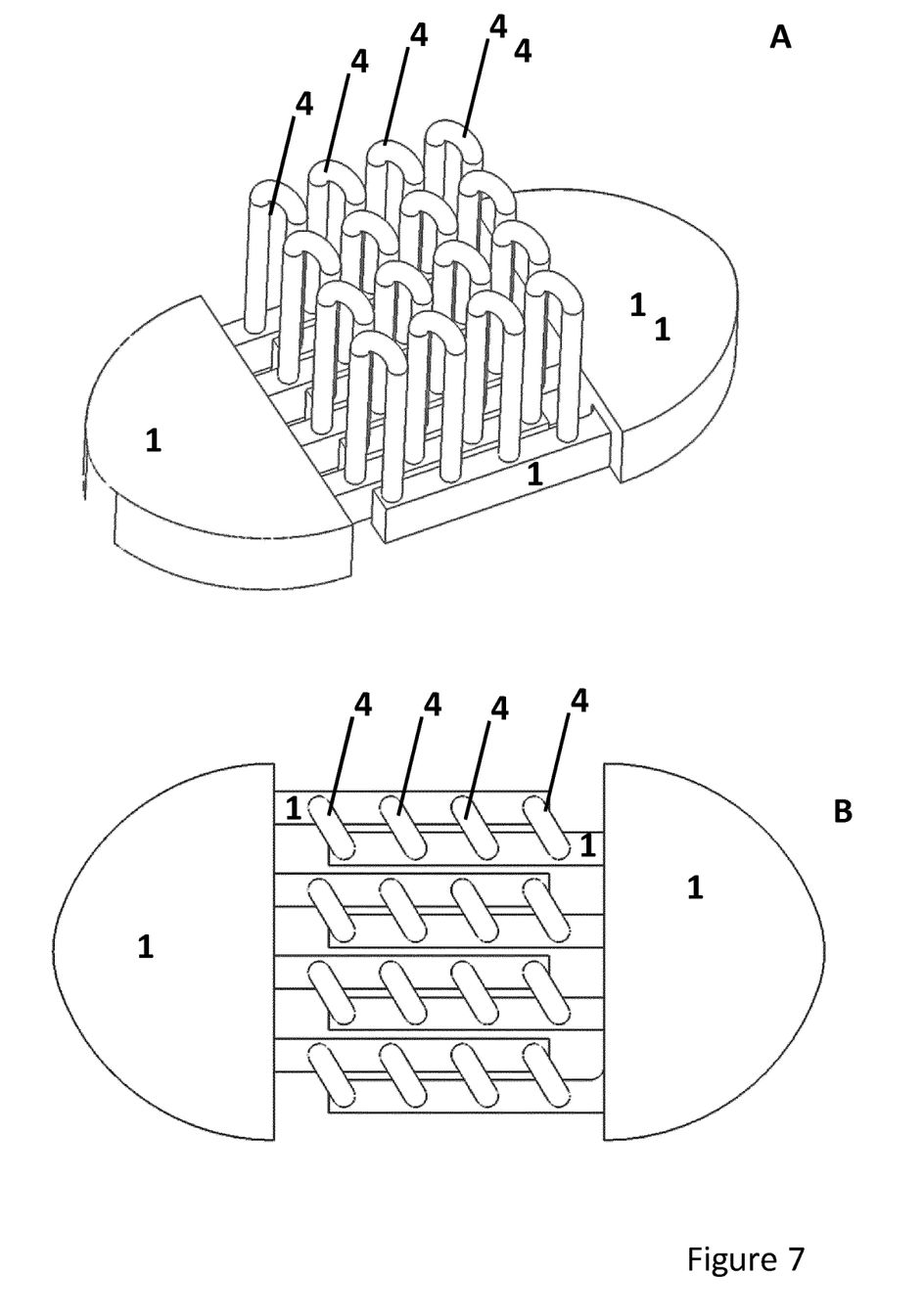
FIG. 7 shows an alternative embodiment of a device of the invention wherein the base plate consists of two elements (one element comprising inlet openings (21) for assembly of channels (31) and one element comprising outlet openings (22) for assembly of channels (32).

For example the opening of an port can be located on the side wall of the base plate, and the medium is distributed via branching channels to the individual inlet openings. Alternative a lumen between the base plate and a support (5) can connect the openings with a port. Such embodiment is shown in FIG. 7.

Figure 6:
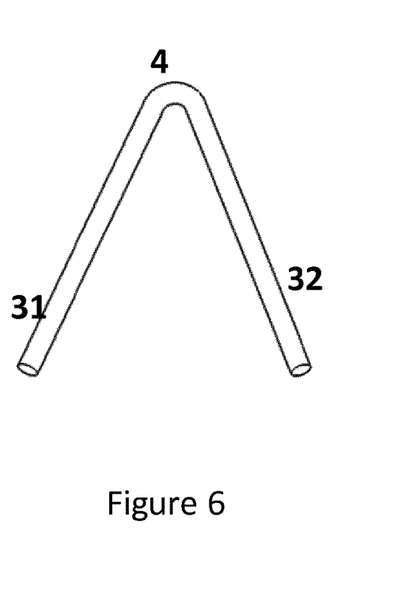
FIG. 6 shows an embodiment of a bent channel with a connection (4).

In FIG. 1A, a base plate consisting of a single oval element is shown. Other shapes (e.g. square or rectangular) are equally possible. The base plate can also be formed by an assembly of adjacent separate elements which distribute medium to and from the inlet and outlet opening. Such an embodiment is shown in FIG. 6, wherein the "fingers" and the circular parts are open at the bottom and fit on a support (5) which contains openings.

FIG. 1B shows a later stage in the production of the device wherein hollow channels (31 and 32) are printed on the inlet and outlet openings. These extend upwards from the base plate (typically vertically like a chimney).

The diameter of the vertical channels can be constant over the entire length or may vary. It is the purpose of the device to mimic a vascular system in those parts of the device which comes into contact with the cells, with respect to diameter and density of the channels. Therefore, the parts on the bottom or top can have a diameter which is wider than the parts which come into contact with the cells.

FIG. 1C shows a further stage in the production of the device wherein connections (4) are made between vertically extending channels. The picture shows a horizontal connection. Variants thereof can be bent or have the shape of a half-circle.

In FIG. 1, the base plate contains a single network, but different network can be printed on one base plate. However a preferred alternative is the use of a support whereon a plurality of base plates with single networks are arranged.

FIG. 1C shows a network wherein the channels are arranged in a grid with a square basis. Other arrangements with an overall rectangular, triangular, oval or other shapes are equally possible.

FIG. 1C shows a network wherein the channels all have an equal height. Alternative configurations may have channels which are shorter at the circumference to generate networks with e.g. a pyramidal or domed like shape. Individual channels may have a length from as short as 100 µm up to 250, 500, 750, 1000, 1500 or 2000 µm. Ranges with any of the above values as lower and upper limit are equally envisaged.

The inner diameter of the channel can range from 5, 10, 20 up to 50, 100, or 200 µm. Ranges with any of the above values as lower and upper limit are equally envisaged.

The outer diameter of the channels may differ. At the sections where the wall is in proximity of the cells, or where in the cells are in contact with the cells, the wall should be sufficiently thin to allow diffusion of nutrients and gasses, and is typically between 5 up to 15, 25 or 50 µm. Near the inlet and outlet opening and at the connection between the two parts of a channel the walls may be thicker to provide more physical support even if this impedes transport through the walls.

The embodiment shown in FIG. 1 shows a regular distribution of pairs of channels which depart vertically from the base plate and have a horizontal connection forming angles of 90°.

To provide sufficient nutrients and oxygen to a cell, the maximum distance between a cell and a tube is preferably less than 500 µm, more preferably at most 200 µm, typically about 240 µm. This can be achieved by a density of between 4 to 25 openings and corresponding vertically extending tubes/mm$^2$.

The plurality of channels can form a network in the form of a cube with dimensions as small as of 0.1×0.1×0.1 mm (i.e. 0,001 mm$^3$).

In a typical embodiment, the cube has inner dimension of 1.2×1.2×1.2 mm. The volume of a network can range e.g. from as small as 0.001 mm$^3$, 0.008 mm$^3$, 0.0125 mm$^3$, 1 mm$^3$, 8 mm$^3$, 125 mm$^3$, 1 cm$^3$, 3.5 cm$^3$, 8 cm$^3$ or 125 cm$^3$.

While the vertical orientation of the channels offers maximal efficiency of the printing process, orientation of the channels can, deviate from 90°, such that the top parts come in each other's proximity whereby the horizontal part is shorter or wider than the distance between two channels at the bottom on the base plate.

The horizontal connection between two channels can be as small as the curve of two channels touching each other at the top, as schematically indicated in FIG. 6.

Other configurations may be envisaged wherein instead of inverse U shaped elements, semi-circular or bent configurations are made to avoid dead volumes at strongly bent sections of a channels, which may impede optimal flow of medium.

Figure 4:
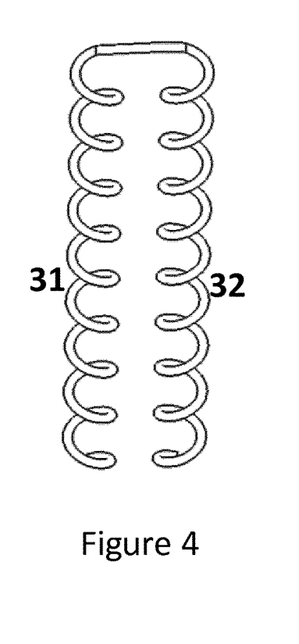
FIG. 4 shows an embodiment of channels with a spiral shape.

Alternatively, to increase the surface between channels and cells the vertical channels can have for example a zig-zig or spiral structure (FIG. 4).

The embodiment in FIG. 1 shows a configuration wherein one channel (31) is connected with one channel (32). Alternatively one channel (31) can be connected with a plurality of channels 32 (or vice versa) such that the medium distributed to a plurality of channels is collected by a single channel (or vice versa).

Figure 5:
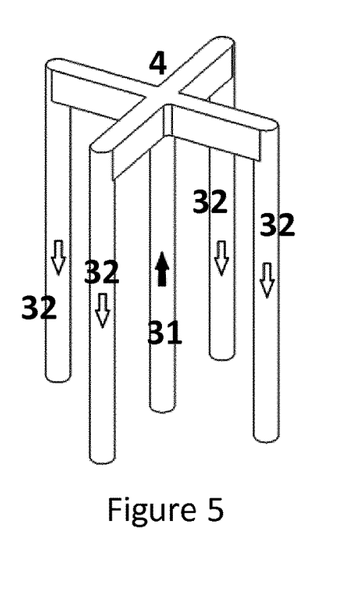
FIG. 5 shows an embodiment of channels wherein one channel (31) delivering medium from the inlet opening is connected to four channels (32) delivering medium to outlet openings.

An schematic version hereof is shown in FIG. 5.

Polymerized hydrogel is a very brittle material. Devices as depicted may have sub-millimeter dimensions and consist of a polymerized hydrogel, which makes them vulnerable for physical damage. In addition to the basic design as described above, additional features can be added to improve the structural integrity of the device.

Figure 2:
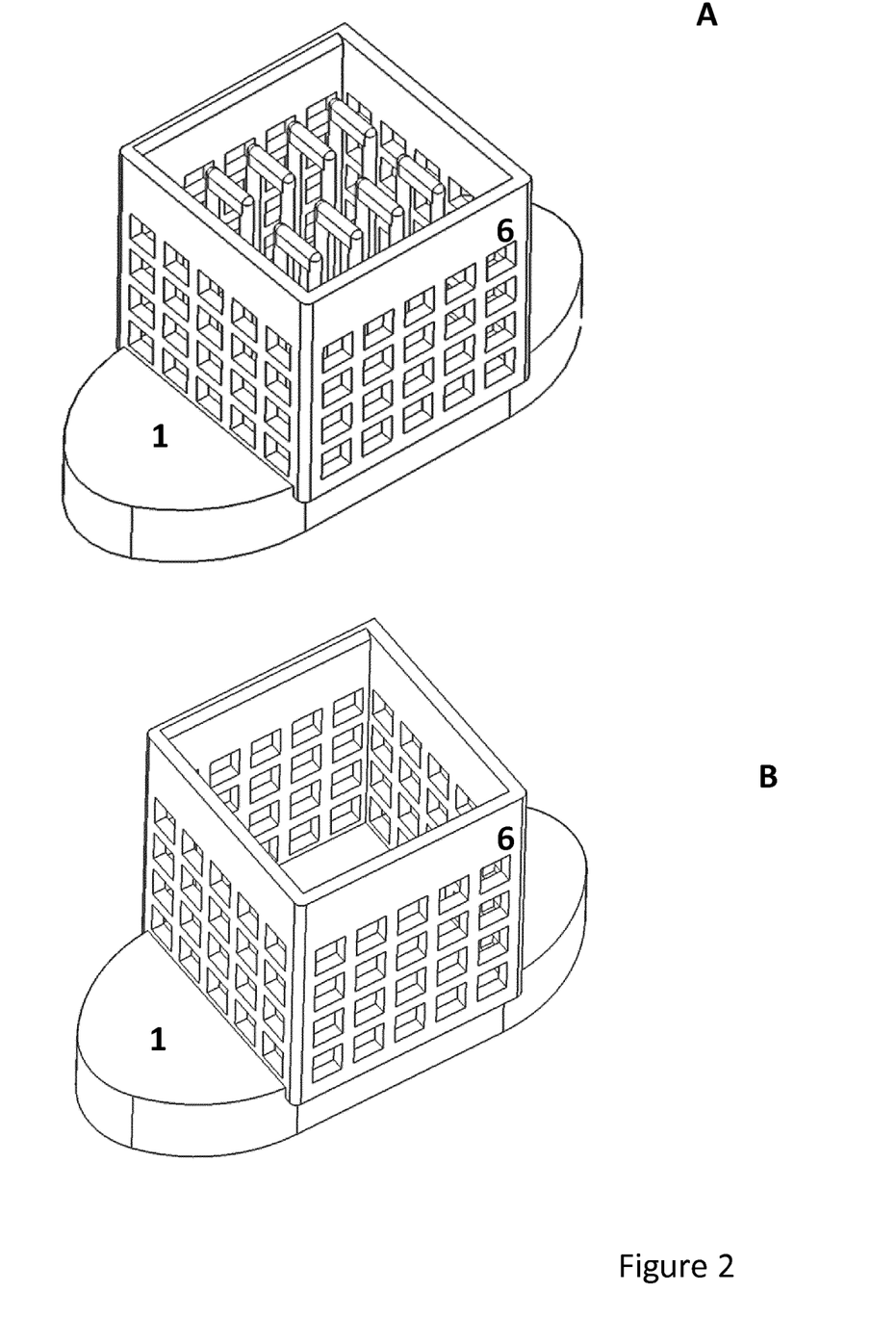
FIG. 2 shows a cell culture device wherein walls (6) form a basket around the channels.

Apart from facilitating medium delivery to and from the channels, the base plate provides structural support which can be increased by making the base plate thicker or larger. In addition one or more walls (6) can be printed on the base plate to shield the channels, or eventually forming a cage around the channels. These walls can form a rectangular or circular cage like structure. The walls can be solid, perforated or grid like to provide sufficient support while at the same time facilitating access of medium to the cultured tissue at the inside. FIG. 2A shows an embodiment wherein simultaneously with the channels a cage has been printed in the same material as the base plate and the channels. In FIG. 2B the channels have been omitted from the drawing to provide a more clear view on the structure.

It is further possible to provide reinforcing elements (8) in-between channels, or between channels and the base plate or between channels and the walls. These can be printed in the same material as the channels, as solid elements without inner volume and in diameters which can be thicker or thinner that the diameter of the channels.

A yet further possibility is the provision of a hydrogel in-between the channels. Such hydrogel typically used as a liquid precursor solution, premixed with cell aggregates and applied drop-wise on top of the channels. The precursor then polymerizes due to enzymatic or physical reaction.

Figure 3:
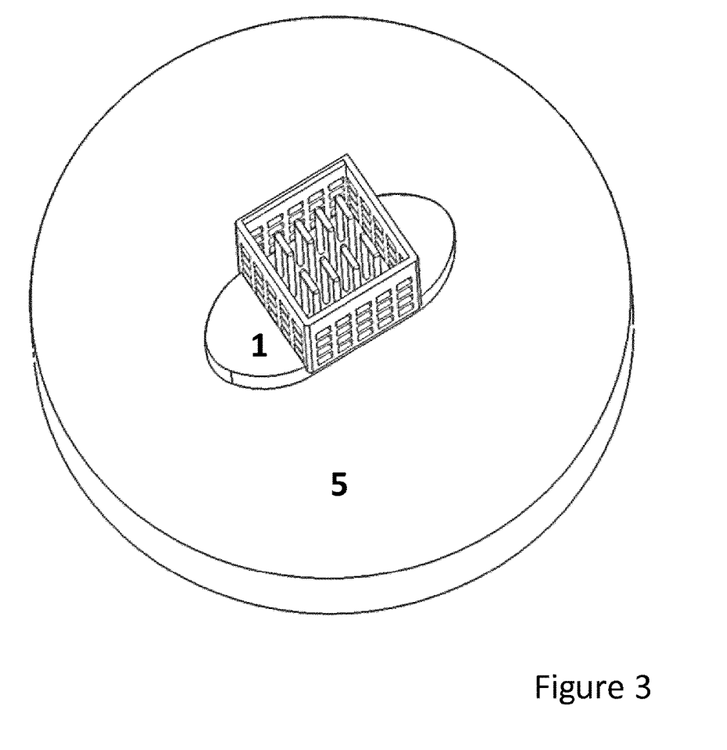
FIG. 3 shows a device with basket (6) which is mounted on a support (5).

In an alternative embodiment, the cell culture device is formed on a rigid support (5) whereby the hydrogel, of which the culture device is fabricated, is cross-linked to the rigid support. (see FIG. 3). A plurality of devices can be arranged on a single support.

Typical materials used for the rigid support are many commercially available resins for DLP/SLA 3D printers. Alternatively, pure monomers like, for example pentaerythritol triacrylate, or any other acrylic-rich molecules can be used with any suitable photo-initiators like, for example, Irgacure 369 or Irgacure 2959.

This allows to manipulate the device via the solid support, in order to insert the device in a bioreactor prior to cells seeding, or to remove the device for analysis of the cell aggregate after cultivation.

The cell culture devices are prepared by stereo-lithographic process.

Stereolithography is a form of additive manufacturing process (3D printing) employing photopolymerization. i.e a process, during which chains of molecules bind, forming polymers (U.S. Pat. No. 4,575,330). As a result of either projecting the patterned light or by direct laser scanning in the bulk of the photopolymerizable liquid monomer solution, the polymers build up and form the body of a three-dimensional structure (Crivello et al. (2014) *Chem. Mater.* 26, 533).

More details on methods for stereo-lithographic printing can be found in e.g. Deubel et al. (2004) *Nature Materials.* 3, 444-447 or Alexandros et al. (2015) *Microelectronic Engineering,* 132, 83-89.

Specifically, a 3-dimensional model of the micro-capillary device is designed. The 3D model then "cut" into twodimensional horizontal slices which are effectively black & white images similar to computer tomography images.

A solution a photo-polymerizable material (of e.g. PEG-diacrylate-based) is placed in a fabrication vat. The first image corresponding to a bottom surface of the microcapillary device is fed to a fabrication system. According to the image, certain locations on the fabrication substrate are illuminated by focused laser, the material is polymerized in the irradiated locations and the first layer of the 3D structure is formed. On the second iteration of the fabrication process, the fabrication substrate moves one step up, the next image is fed to the system and the second layer is formed. Due to presence of acrylic moieties exposed at the surface of the first layer, the second generated layer cross-links to the previous layer during laser irradiation, which enables formation of a solid 3-dimensional structure.

The rest of the images are fed sequentially to a fabrication system and the base plate, channels, optional reinforcing elements and walls are generated in a layer-by-layer fashion.

Generally, the fabrication vast contains a support with crosslinkable groups, whereby the printing of the first layer crosslinks the phopolymerised material to the support.

An overview of materials suitable in the methods and device of the present invention are reviewed in US20160002368 and comprise polyacrylamides; polyethyleneglycols containing repetitive patterns derived from polymerization of acrylate or methacrylate compounds; polysaccharides, possibly modified (for example modified polysaccharides containing repetitive patterns derived from polymerization of acrylate compounds); (co)polymers derived from polymerization of diacrylate and/or (meth)acrylate compounds; polyvinyl alcohols containing repetitive patterns derived from polymerization of acrylate or methacrylate compounds; dextranes containing repetitive patterns derived from polymerization of (meth)acrylate compounds; polypropylene fumarates and derivatives of them, such as poly(propylene-co-ethyleneglycol fumarate); and combinations of these materials; polyacrylamides; polyethyleneglycols containing repetitive patterns derived from polymerization of acrylate or methacrylate compounds; polysaccharides, possibly modified (for example modified polysaccharides containing repetitive patterns derived from polymerization of acrylate compounds); (co)polymers derived from polymerization of diacrylate and/or (meth)acrylate compounds; polyvinyl alcohols containing repetitive patterns derived from polymerization of acrylate or methacrylate compounds; dextranes containing repetitive patterns derived from polymerization of (meth)acrylate compounds; polypropylene fumarates and derivatives of them, such as poly(propylene-co-ethyleneglycol fumarate); and combinations of these materials. The polymerizable compound(s) may be monomers or oligomers or polymers comprising at least one polymerizable function The polymerizable compounds used can thus be: acrylamide monomers to obtain polyacrylamides; acrylate and/or methacrylate compounds put in the presence of polyethyleneglycols to obtain polyethyleneglycols comprising repetitive patterns derived from polymerization of acrylate and/or methacrylate compounds, the polymerizable function being located at these acrylate and/or methacrylate compounds; acrylate monomers (that will be put in the presence of polysaccharide compounds) to obtain polysaccharides modified by acrylate compounds; diacrylate and/or (meth)acrylate monomers to obtain (co)polymers derived from the polymerization of diacrylate and/or (meth)acrylate compounds; polyvinyl alcohols put in the presence of acrylate and/or methacrylate compounds to obtain polyvinyl alcohols containing repetitive patterns derived from the polymerization of acrylate or methacrylate compounds of polyvinyl alcohols, the polymerizable function being located at these acrylate and/or methacrylate compounds; (meth)acrylate monomers put in the presence of dextrane compounds, to obtain dextranes containing repetitive patterns derived from polymerization of (meth)acrylate compounds; propylene fumarate monomers, to obtain polypropylene fumarates and derivatives of them. Acrylate and/or methacrylate compounds put in the presence of polyethyleneglycols to obtain polyethyleneglycols comprising repetitive patterns derived from polymerization of acrylate and/or methacrylate compounds, the polymerizable function being located at these acrylate and/or methacrylate compounds; acrylate monomers (that will be put in the presence of polysaccharide compounds) to obtain polysaccharides modified by acrylate compounds; diacrylate and/or (meth)acrylate monomers to obtain (co)polymers derived from the polymerization of diacrylate and/or (meth)acrylate compounds; polyvinyl alcohols put in the presence of acrylate and/or methacrylate compounds to obtain polyvinyl alcohols containing repetitive patterns derived from the polymerization of acrylate or methacrylate compounds of polyvinyl alcohols, the polymerizable function being located at these acrylate and/or methacrylate compounds; (meth)acrylate monomers put in the presence of dextrane compounds, to obtain dextranes containing repetitive patterns derived from polymerization of (meth)acrylate compounds; propylene fumarate monomers, to obtain polypropylene fumarates and derivatives of them. Photopolymerization initiators that can be used may be initiators of the aromatic ketones family, acridine compounds, fluorone compounds.

Example 1

As a proof of principle a device of 2.4×1.2 mm and 1.5 mm height was made from a solution of PEG-diacrylate using Nanoscribe Photonic Professional GT. The device contains 8 channels with an-inverse U shape configuration. The walls of the channel have a thickness of 10 μm. The internal diameter of the channels is 40 μm.

The channels are surrounding by walls with a thickness of 70 μm.

Figure 8:
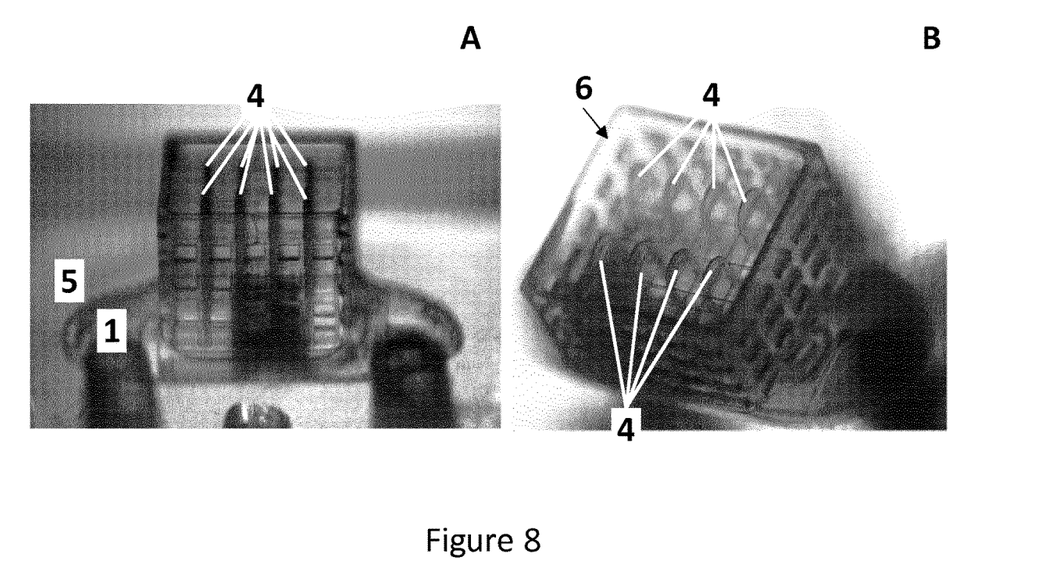
FIG. 8 shows a device with two rows of four channels with inverse U-shape, surrounded by a basket. Figure BA.

The device is shown in FIG. 8.

The device is seeded with paraxial mesoderm organoids at very early stage of development, which are precursors of skeletal muscle tissue. The organoids were differentiated from human induced pluripotent stem cells.

Figure 9:
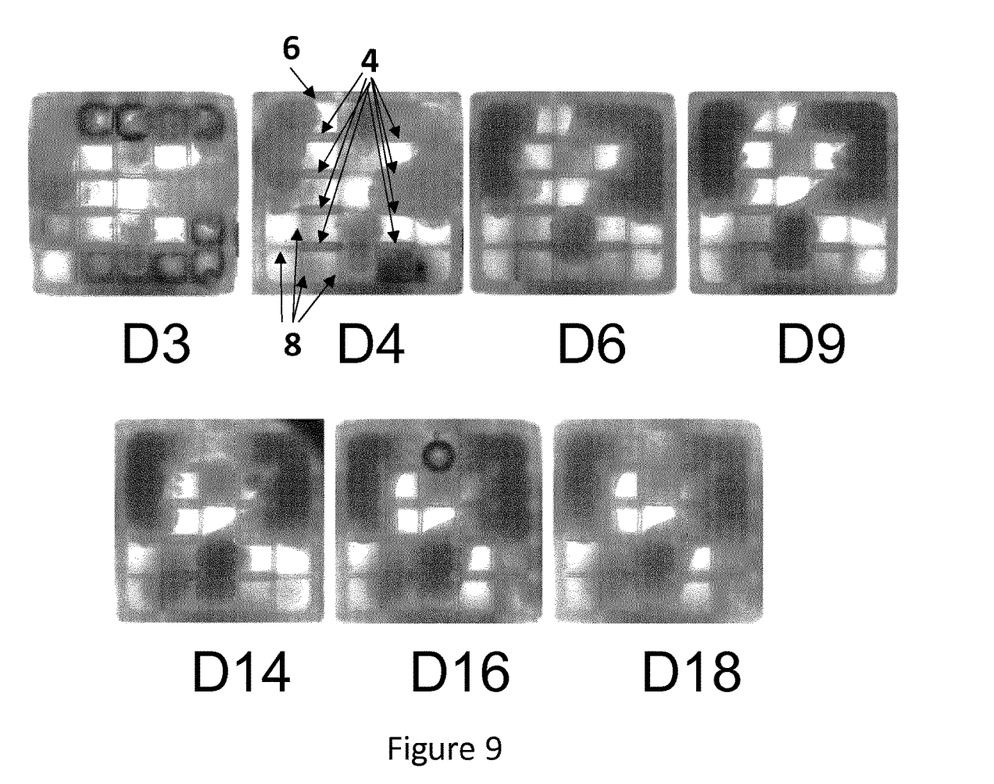
FIG. 9 shows top views of the device of FIG. 8, wherein organoids are seeded. Reinforcing elements (8) connect the walls of the channels. The elements do not contain or transport medium. The device has been seeded with organoids at day 0. Organoid growth from day 3 (D3) to day 18 (D18) fills the space inbetween the channels.

FIG. 9 shows a top view of the device (3 up to 18 days after seeding) wherein the lumen between the channels becomes filled with cells.

The invention claimed is:

1. A device for the culture of cellular aggregates, the device comprising:
    a base plate with inlet and outlet openings for delivery and removal of media, wherein the inlet and outlet openings are in fluidic connection with respectively inlet and outlet ports in the base plate; and
    a plurality of channels of a biocompatible liquid- and gas-permeable material, wherein each of the channels is connected at one end to a respective inlet opening of the base plate and at another end to a respective outlet opening of the base plate,
wherein each channel extends at one end upwards from the respective inlet opening, and extends at the other end upwards from the respective outlet opening.

2. The device according to claim 1, wherein the channels extend vertically upwards from the base plate.

3. The device according to claim 1, wherein the channels have an inverse U-shape conformation.

4. The device according to claim 1, further comprising reinforcements between the channels.

5. The device according to claim 1, further comprising re-enforcing structures surrounding the channels.

6. The device according to claim 1, wherein the biocompatible liquid- and gas-permeable material is a photopolymerised hydrogel.

7. The device according to claim 1, wherein the plurality of channels form a network with a volume from 0.1 mm$^3$ to 5 cm$^3$ mimicking a vascular network.

8. The device according to claim 1, wherein the channels have an internal diameter of from 5 m to 200 m.

9. The device according to claim 1, wherein the base plate is attached to a support, wherein channels for the supply and removal of liquids are in fluidic connection with outlet and inlet ports on the base plate.

10. The device according to claim 9, wherein the attachment of the base plate and the support is obtained via crosslinking between the material of the base plate and the material of the support.

11. The device according to claim 9, wherein the attachment of the base plate and the support is obtained via a male-female locking mechanism, and wherein locking results from the swelling of the male part upon hydration in aqueous environments.

12. The device according to claim 1, further comprising reinforcing elements connecting walls of the channels, wherein the reinforcing elements do not contain or transport medium.

* * * * *

UNITED STATES PATENT AND TRADEMARK OFFICE
CERTIFICATE OF CORRECTION

PATENT NO. : 12,146,128 B2
APPLICATION NO. : 17/253803
DATED : November 19, 2024
INVENTOR(S) : Sergii Grebeniuk and Adrian Ranga It is certified that error appears in the above-identified patent and that said Letters Patent is hereby corrected as shown below:

In the Specification

In Column 3, Line(s) 7, delete "opining" and insert --opening--, therefor.

In Column 3, Line(s) 48, delete "FIG. 21" and insert --FIG. 2B--, therefor.

In Column 4, Line(s) 25, delete "plates" and insert --plate--, therefor.

In Column 4, Line(s) 38, before "port", delete "an" and insert --a--, therefor.

In Column 5, Line(s) 43, delete "0,001 mm³" and insert --0.001 mm³--, therefor.

In Column 5, Line(s) 44, before "inner dimension", insert --an--, therefor.

In Column 7, Line(s) 53, after "function", insert --.--.

In the Claims

In Column 9, Claim 8, Line 2, delete "5 m to 200 m" and insert --5 μm to 200 μm--, therefor.

Signed and Sealed this
Thirtieth Day of September, 2025

John A. Squires
*Director of the United States Patent and Trademark Office*